United States Patent [19]

Hoelderich et al.

[11] Patent Number: 4,812,593
[45] Date of Patent: Mar. 14, 1989

[54] PREPARATION OF BIFUNCTIONAL COMPOUNDS

[75] Inventors: Wolfgang Hoelderich, Frankenthal; Norbert Goetz, Worms; Leopold Hupfer, Friedelsheim, all of Fed. Rep. of Germany

[73] Assignee: BASF Aktiengesellschaft, Ludwigshafen, Fed. Rep. of Germany

[21] Appl. No.: 82,127

[22] Filed: Aug. 6, 1987

[30] Foreign Application Priority Data

Aug. 27, 1986 [DE] Fed. Rep. of Germany ....... 3629119
Jan. 16, 1987 [DE] Fed. Rep. of Germany ....... 3701113

[51] Int. Cl.$^4$ .............................................. C07C 69/73
[52] U.S. Cl. ................................... 560/183; 560/186; 560/187; 568/392; 568/460; 568/465; 568/486
[58] Field of Search .................. 560/183, 186, 187; 568/392, 460, 465, 485, 486; 502/61, 73, 74, 75, 77, 78, 79, 208, 214

[56] References Cited

U.S. PATENT DOCUMENTS

| | | | |
|---|---|---|---|
| 1,738,659 | 12/1929 | Maude | 568/460 |
| 2,459,076 | 1/1949 | Hultquist | 568/603 |
| 2,465,586 | 3/1949 | Gaspar | 568/433 |
| 2,571,212 | 10/1951 | Croxall et al. | 560/186 |
| 2,815,384 | 12/1957 | Guest et al. | 568/459 |
| 2,816,109 | 12/1957 | Sletzinger et al. | 544/258 |
| 2,870,221 | 1/1959 | Hall et al. | 568/598 |

FOREIGN PATENT DOCUMENTS 498973 1/1934 United Kingdom ................ 568/392
832162 4/1960 United Kingdom ................ 568/392

*Primary Examiner*—Bruce D. Gray
*Attorney, Agent, or Firm*—Keil & Weinkauf

[57] ABSTRACT

Bifunctional compounds of the formula

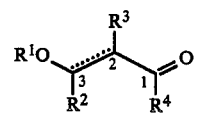

where $R^1$, $R^2$ and $R^3$ are each alkyl of 1 to 6 carbon atoms, $R^2$ and $R^3$ may furthermore be hydrogen, $R^2$ is furthermore alkoxy and $R^4$ is hydrogen, alkyl of 1 to 6 carbon atoms or alkoxy, and a double bond may be present between carbon atoms 2 and 3, are prepared by converting a tetraalkoxyalkane or a dialkoxyalkanoate of the formulae

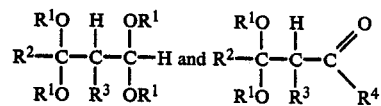

where $R^1$, $R^2$, $R^3$ and $R^4$ have the above meanings, in the presence of a catalyst, such as a zeolite, in particular one of the pentasil type, and/or a phosphate and/or phosphoric acid on a carrier.

12 Claims, No Drawings

PREPARATION OF BIFUNCTIONAL COMPOUNDS

The present invention relates to a process for the catalytic preparation of bifunctional compounds from tetraalkoxyalkanes or dialkoxyalkanoates.

Bifunctional compounds are as a rule very useful building blocks in organic synthesis. Particularly interesting compounds are those which have simple protective groups or groups of different or graded reactivity, so that each function can be subjected to control reactions.

This important class of substances includes, for example in the case of the $C_3$ compounds, the Monoacetals of malonaldehyde or 3-alkoxyacroleins (synthesis (1985), 592-595). Synthesis variants such as the ozonolysis of 1,1-dialkoxy-3-alkenes (C.A. (1961) 55, 20926) or addition reactions of alcohols with propargyl aldehyde (Skoldinov et al., Zh. Org. Chim. (1968), 183, and (1970), 422) cannot be used to prepare these compounds by an industrially feasible method because the intermediates are difficult to obtain.

1,1,3-trialkoxypropenes can be prepared from acrolein. The disadvantage of this procedure is that the synthesis of the 1,1,3-trialkoxypropenes has to be carried out via several stages, and it is only possible to prepare the halomalonaldehyde monoacetals by a partial hydrolysis of the acetals, after halogenation has been carried out beforehand (U.S. Pat. Nos. 2,816,109, 2,815,384 and 2,870,221, Price Moos, J. Am. Chem. Soc. 67 (1945), 207, McElvain and Morris, J. Am. Chem. Soc. 73 (1950), 206 and Rothstein and Whiteley, Soc. (1953), page 4015).

Another possible method of synthesising malonaldehyde derivatives is to combine readily available $C_1$ and $C_2$ compounds. U.S. Pat. No. 2,465,586 describes the preparation of such compounds by condensation of formic acid derivatives with acetalaldehyde acetals; however, the condensation is carried out in the presence of large amounts of metallic sodium or sodium alcoholates and gives poor yields.

The partial hydrolysis of tetraalkoxypropanes to monoacetals of malonaldehyde or 3-alkoxyacrolein (Breitmeier and Gassenmann, Chem. Ber. 104 (1971), 665-667, and Ruegg et al., Helv. Chim. Acta 42 (1959), 847-853) generally gives mixtures which are difficult to purify since the tetraalkoxypropanes used as starting materials and the 3-alkoxyacroleins formed as reaction products have virtually identical boiling points, so that separation by distillation is impossible (Eskenazi and Maitte, Bull. Soc. Chem. Fr. 1976, 995-998). In order to obtain the pure compound, it is necessary to prepare an alkali metal salt of the enol compound as an intermediate and then to derivatize this further by alkylation or acylation (Eskenazi and Maitte, Bull. Soc. Chim. Fr. 1976, 995-998, and Maddaluno and D'Angelo, Tetrahedron Lett. (1983), 895-898). Pure 3-alkoxyacryoleins are obtained if tetraalkoxypropanes are heated with cyclic anhydrides, eg. maleic anhydride, succinic anhydride, glutaric anhydride or phthalic anhydride, at from 150° to 180° C. The disadvantage of this process is the fact that the cyclic anhydrides are required in a stoichiometric amount and that the corresponding esters of maleic acid, succinic acid, etc. are inevitably produced in this process.

We have found that the disadvantages of the known processes are avoided, and bifunctional compounds of the formula (I)

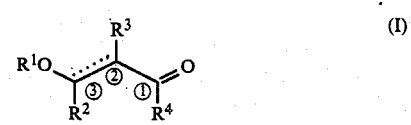

where $R^1$, $R^2$ and $R^3$ are each alkyl of 1 to 6 carbon atoms, $R^2$ and $R^3$ may furthermore be hydrogen, $R^2$ may furthermore be alkoxy and $R^4$ is hydrogen, alkyl of 1 to 6 carbon atoms or alkoxy, and a double bond may be present between carbon atoms 2 and 3, are obtained, if a tetraalkoxyalkane of the formula II or a dialkoxyalkanoate of the formula III

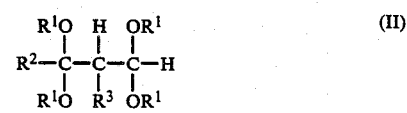

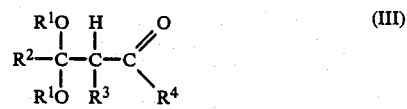

where $R^1$, $R^2$, $R^3$ and $R^4$ have the above meanings, is converted in the presence of a zeolite and/or a phosphate and/or phosphoric acid on a carrier as catalysts.

The preparation of the tetraalkoxyalkanes and dialkoxyalkanoates used as starting materials is disclosed in, for example, U.S. Pat. No. 2,459,076.

Suitable catalysts for the purposes of the present invention are in general zeolites of the pentasil type, such as aluminum silicate zeolites, borosilicate zeolites, iron silicate zeolites and zeolites of the faujasite type.

The zeolites may be doped with, for example, alkali metals, transition metals or rare earth metals.

However, phosphates of the elements B, Al, Zr, Fe or Sr or mixtures of these may also be used as catalysts. For example, phosphates prepared by a hydrothermal process are also suitable catalysts, eg. hydrothermal aluminum phosphates, silicon aluminum phosphates or silicon iron aluminum phosphates. Phosphoric acid on carriers can also be used as catalysts.

The zeolites are advantageously used in the acidic form as catalysts for the novel process. Zeolites are crystalline aluminum silicates which have a highly ordered structure comprising a rigid three-dimensional network of $SiO_4$ and $AlO_4$ tetrahedra which are linked by common oxygen atoms. The ratio of Si and Al atoms to oxygen is 1:2. The electrovalency of the aluminum-containing tetrahedra is balanced by inclusion of cations in the crystal, for example an alkali metal or hydrogen ion. Cation exchange is possible. The spaces between the tetrahedra are occupied by water molecules prior to dehydration by drying or calcination.

In the zeolites, other elements, such as B, Ga, Fe, Cr, V, As, Sb, Bi or Be or mixtures of these, may be incorporated into the framework instead of aluminum, or the silicon can be replaced by a tetravalent element such as Ge, Ti, Zr or Hf.

Depending on their structure, zeolites are divided into various groups. For example, the zeolite structure is formed by chains of tetrahedra in the mordenite group or by layers of tetrahedra in the Chabasite group, whereas in the faujasite group the tetrahedra are arranged to form polyhedra, for example a cubooctahedron, which is composed of 4-membered rings and 6-membered rings. Depending on the way in which the cubooctahedra are linked, giving rise to cavities and pores of different sizes, a distinction is made between zeolites of type A, L, X and Y.

Catalysts which are suitable for the novel process are zeolites of the mordenite group and fine-pored zeolites of the erionite or chabasite type or zeolites of the faujasite type, for example Y, X or L zeolites. This group of zeolites also includes the ultrastable zeolites of the faujasite type, ie. dealuminated zeolites. Processes for the preparation of such zeolites have frequently been described.

Particularly advantageous zeolites are those of the pentasil type. The common basic building block of these is a 5-membered ring composed of $SiO_4$ tetrahedra. They have a high $SiO_2/Al_2O_3$ ratio and pore sizes between those of the zeolites of type A and those of type X or Y.

These zeolites may have different chemical compositions. They are aluminosilicate, borosilicate, iron silicate, beryllium silicate, gallium silicate, chromium silicate, arsenic silicate, antimony silicate and bismuth silicate zeolites or mixtures of these, and aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$ and a silicon component, preferably finely divided silica, in aqueous amine solution, in particular in a polyamine, such as 1,6-hexanediamine or 1,3-propanediamine or triethylenetetramine solution, with or, in particular, without the addition of an alkali metal or an alkaline earth metal, at from 100° to 220° C. under autogenous pressure. The isotactic zeolites according to European Patents 34,727 and 46,504 are also included here. The aluminosilicate zeolites obtained have an $SiO_2/Al_2O_3$ ratio of from 10 to 40,000, depending on the amounts of starting materials chosen. These aluminosilicate zeolites can be synthesised in an ether medium, such as diethylene glycol dimethyl ether, in an alcoholic medium, such as methanol or 1,4-butanediol, or in water.

Borosilicate zeolites can be synthesised, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution, with or, in particular, without the ddition of an alkali metal or an alkaline earth metal. The isotactic zeolites according to European Patents 34, 727 and 46,504 are also included here. Such borosilicate zeolites can also be obtained if the reaction is carried out in solution in an ether, eg. diethylene glycol dimethyl ether, or in alcoholic solution, eg. in 1,6-hexanediol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular in 1,6-hexanediamine, with or without the addition of an alkali metal or an alkaline earth metal, at from 100° to 200° C. under autogenous pressure.

The silicon-rich zeolites ($SiO_2/Al_2O_3 \geq 10$) which can be used according to the invention include the various ZSM types, ferrierite, NU-1 and Silicalit ®.

The aluminosilicate, borosilicate and iron silicate zeolites thus prepared can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After. the molding procedure, the extrudates or pellets are dried for 16 hours at 110° C. and calcined for 16 hours at 500° C.

Advantageous catalysts are also obtained if the aluminosilicate or borosilicate zeolite isolated is molded directly after the drying procedure and subjected to calcination only after being molded. The aluminosilicate and borosilicate zeolites prepared can be used in pure form, without a binder, as extrudates or pellets, examples of extrusion or peptizing assistants used being ethyl cellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example, in the Na form, the latter can be converted completely or partially to the desired H form by ion exchange, for example with ammonium ions, followed by calcination, or by treatment with an acid.

If, when the zeolite catalysts are used according to the invention, deactivation due to coking occurs, it is advisable to regenerate the zeolites by burning off the coke deposit with air or with an air/$N_2$ mixture at from 400° to 550° C., preferably 500° C. As a result, the zeolites recover their initial activity.

By precoking, it is possible to adjust the activity of the catalyst to give optimum selectivity for the desired reaction product.

In order to obtain very high selectivity, high conversions and long lives, it is advantageous to modify the zeolites. In a suitable method for modifying the catalysts, for example, the unmolded or molded zeolites are doped with metal salts by ion exchange or impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4–8, such as Ti, Zr, V, Nb, Cr, Mo, W, Mn, Re, Fe, Ru, Os, Co, Rh, Sr, Ni, Pd or Pt, transition metals of subgroups 1 and 2, such as Cu, Ag or Zn, or rare earth metals, such as La, Ce, Pr, Nd, Er, Yb or U.

The doping is advantageously carried out by initially taking the molded zeolites in a riser tube and passing over an aqueous or ammoniacal solution of a halide or nitrate of the metals described above, at from 20° to 100° C. Ion exchange of this type can be carried out on the hydrogen, ammonium and alkali metal form of the zeolite. Another possible method of applying the metals to the zeolites entails impregnating the zeolite material, for example with a halide, a nitrate or an oxide of the metals described above, in aqueous, alcoholic or ammoniacal solution. Both ion exchange and impregnation are followed by one or more drying procedures and, if desired, repeated calcination.

In a possible embodiment, for example, $Cu(NO_3)_2 \times 3 H_2O$ or $Ni(NO_3)_2 \times 6 H_2O$ or $Ce(NO_3)_3 \times 6 H_2O$ or $La(NO_3)_3 \times 6 H_2O$ or $Cs_2CO_3$ is dissolved in water, and this solution is used to impregnate the molded or unmolded zeolite for a certain time, for example 30 minutes. Any supernatant solution is freed from water in a rotary evaporator. The impregnated zeolite is then dried at about 150° C. and calcined at about 550° C. This impregnation process can be carried out several times in succession in order to obtain the desired metal content.

It is also possible to prepare an aqueous $Ni(NO_3)_2$ solution or ammoniacal $Pd(NO_3)_2$ solution and to suspend the pure powdered zeolite therein at from 40° to 100° C. for about 24 hours, while stirring. After filtering off, drying at about 150° C. and calcining at about 500° C., the zeolite material thus obtained can be further processed, with or without a binder, to give extrudates, pellets or fluidizable material.

The zeolite in the H form, ammonium form or alkali metal form can be subjected to ion exchange by initially taking the zeolite in the form of extrudates or pellets in a column and circulating over it, for example, an aqueous $Ni(NO_3)_2$ solution or ammoniacal $Pd(NO_3)_2$ solution at slightly elevated temperatures of from 30° to 80° C. for from 15 to 20 hours. The zeolite is then washed thoroughly with water, dried at about 150° C. and calcined at about 550° C. In the case of some metal-doped zeolites, for example Pd-, Cu- or Ni-doped zeolites, after-treatment with hydrogen is advantageous.

In another possible method of modification, the molded or unmolded zeolite material is treated with an acid, such as hydrochloric acid, hydrofluoric acid or phosphoric acid and/or steam. In an advantageous procedure, for example, the zeolite in powder form is treated with 1 N phosphoric acid for 1 hour at 80° C. After the treatment, it is washed with water, dried at 110° C. for 16 hours and calcined at 500° C. for 20 hours. In another procedure, the zeolite, before or after being molded with a binder, is treated, for example, for from 1 to 3 hours at from 60° to 80° C. with a 3-25, in particular 12-20, % strength by weight aqueous hydrochloric acid. The zeolite treated in this manner is then washed with water, dried, and calcined at from 400° to 500° C.

In a particular embodiment of the acid treatment, the zeolite material, before being molded, is treated at elevated temperatures with hydrofluoric acid, which is generally used in the form of 0.001-2 N, preferably 0.05-0.5 N hydrofluoric acid, for example by refluxing for in general from 0.5 to 5, preferably from 1 to 3, hours. After the zeolite material has been isolated, for example by filtering off and washing thoroughly, it is advantageously dried, for example at from 100° to 160° C., and calcined at in general from 450° to 600° C. In another preferred embodiment of the acid treatment, the zeolite material is molded with a binder and then treated at elevated temperatures, advantageously from 50° to 90° C., preferably from 60° to 80° C., for from 0.5 to 5 hours, preferably with from 12 to 20% strength by weight hydrochloric acid. Advantageously, zeolite material is then washed thoroughly, dried at from 100° to 160° C. and calcined at from 450° to 600° C. An HF treatment can also be followed by an HCl treatment.

In another procedure, zeolites can be modified by applying phosphorus compounds, such as trimethyl phosphate, trimethoxyphosphine or primary, secondary or tertiary sodium phosphate.

The treatment with primary sodium phosphate has proven particularly advantageous. In this procedure, the zeolites in the form of extrudates, pellets or fluidizable material are impregnated with aqueous $NaH_2PO_4$ solution, dried at 110° C. and calcined at 500° C.

Other catalysts for the preparation of bifunctional compounds of the formula (I) from tetraalkoxyalkanes of the formula (II) or dialkoxyalkanoates of the formula (III) are phosphates, in particular aluminum phosphate, silicon aluminum phosphate, silicon iron aluminum phosphate, cerium phosphate, zirconium phosphate, boron phosphate, iron phosphate or mixtures of these.

For the novel process, particularly under hydrothermal conditions, the aluminum phosphate catalysts used are synthetic aluminum phosphates. Examples of suitable aluminum phosphates are APO-5, APO-9, APO-11, APO-12, APO-14, APO-21, APO-25, APO-31 and APO-33.

For example, $AlPO_4$-5 (APO-5) is synthesised by mixing orthophosphoric acid with pseudoboehmite (Catapal SB ®) in water to give a homogeneous mixture; tetrapropylammonium hydroxide is added to this mixture, after which the reaction is carried out at about 150° C. for from 20 to 60 hours under autogenous pressure in an autoclave. The $AlPO_4$ is filtered off, dried at from 100° to 160° C. and calcined at from 450° to 550° C.

$AlPO_4$-9 (APO-9) is likewise synthesised from orthophosphoric acid and pseudoboehmite, but in aqueous DABCO (1,4-diazabicyclo(2,2,2)octane) solution at about 200° C. under autogenous pressure for from 200 to 400 hours. If ethylenediamine is used instead of the DABCO solution, APO-12 is obtained.

$AlPO_4$-21 (APO-21) is synthesised from orthophosphoric acid and pseudoboehmite in aqueous pyrrolidone solution at from 150° to 200° C. under autogenous pressure for from 50 to 200 hours.

For the novel process, it is also possible to use known silicon aluminum phosphates, such as SAPO-5, SAPO-11, SAPO-31 and SAPO-34. These compounds are prepared by crystallization from an aqueous mixture at from 100° to 250° C. and under autogenous pressure for from 2 hours to 2 weeks, the reaction mixture consisting of a silicon, aluminum and phosphorus component being converted to aqueous organic amine solutions.

For example, SAPO-5 is obtained by mixing a suspension of $SiO_2$ in aqueous tetrapropylammonium hydroxide solution with an aqueous suspension of pseudoboehmite and orthophosphoric acid and then carrying out the reaction at from 150° to 200° C. for from 20 to 200 hours under autogenous pressure in a stirred autoclave. The powder is filtered off and then dried at from 110° to 160° C. and calcined at from 450° to 550° C.

Boron phosphates as catalysts for the novel process can be prepared, for example, by mixing and kneading concentrated boric acid and phosphoric acid, followed by drying and calcination in an inert gas, air or steam atmosphere at from 250° to 650° C., preferably from 300° to 500° C.

Phosphoric acid is applied to $SiO_2$, $Al_2O_3$ or pumice carriers, for example by impregnation or spraying. A catalyst containing phosphoric acid can be obtained, for example, by impregnating $SiO_2$ with $H_3PO_4$, $NaH_2PO_4$ or $Na_2HPO_4$ solution and then drying and calcining the product. However, phosphoric acid can also be sprayed together with silica gel in a spray tower; this is followed by drying and in general calcination. Phosphoric acid can furthermore be sprayed onto the carrier in an impregnating mill.

The catalysts described here can be used alternatively in the form of 2-4 mm extrudates, pellets of 3-5 mm diameter or chips having particle sizes of from 0.1 to 0.5 mm, or as a fluidized catalyst.

The reaction conditions generally chosen for the novel conversion in the gas phase, which is preferably used, are from 100° to 500° C., in particular from 200 to 400° C., and a WHSV of from 0.1 to 20 h$^{-1}$, in particular from 0.5 to 5 h$^{-1}$ (g of starting mixture per g of catalyst per hour).

It is also possible to carry out the reaction in the liquid phase, for example by the suspension, trickle-bed or liquid phase procedure, at from 50° to 200° C.

The process is generally carried out under atmospheric pressure or, depending on the volatility of the starting compound, under reduced or superatmospheric pressure, either continuously or batchwise.

Sparingly volatile or solid starting materials are used in dissolved form, for example in solution in tetrahydrofuran, toluene or petroluem ether. In general, it is possible to dilute the starting material with such solvents or with inert gases such as $N_2$, Ar or steam.

After the reaction, the products obtained are isolated from the reaction mixture by a conventional method, for example by distillation; unconverted starting mixture is, if necessary, recycled to the reaction.

It is particularly advantageous to separate the gaseous reaction products immediately into the individual components. Separation of this type can be carried out, for example, in a fractionation column. By means of the separation, it is possible to suppress a reverse reaction and to obtain a higher conversion.

EXAMPLES 1 TO 17

The reactions in the gas phase are carried out under isothermal conditions in a tube reactor (coil, internal diameter 0.6 cm, length 90 cm) in the course of not less than 6 hours. The reaction products are isolated by a conventional method and characterized. The reaction products and the starting materials are determined quantitatively by gas chromatography, the GC analyses being carried out after 6 hours.

The catalysts used in each case are:

Catalyst A

A borosilicate zeolite of the pentasil type is prepared by a hydrothermal synthesis from 640 g of finely divided $SiO_2$, 122 g of $H_3BO_3$ and 8,000 g of an aqueous 1,6-hexanediamine solution (weight ratio of the mixture 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$.

This material is molded with a molding assistant to prepare 2 mm extrudates, which are dried at 100° C. for 16 hours and calcined at 500° C. for 24 hours.

Catalyst B

An aluminosilicate zeolite of the pentasil type is prepared under hydrothermal conditions from 65 g of finely divided $SiO_2$ and 20.3 g of $Al_2(SO_4)_3 \times 18 H_2O$ in 1 kg of an aqueous 1,6-hexanediamine solution (weight ratio of the mixture 50:50) under autogenous pressure and at 150° C. in a stirred autoclave. The crystalline reaction product is filtered off, washed thoroughly, dried at 110° C. for 24 hours and then calcined at 500° C. for 24 hours. This aluminosilicate zeolite contains 91.6% by weight of $SiO_2$ and 4.6% by weight of $Al_2O_3$. The catalyst is molded to give 2 mm extrudates, which are dried at 110° C. for 16 hours and calcined at 500° C. for 24 hours.

Catalyst C

Catalyst C is obtained by impregnating the extrudates of catalyst A with an aqueous $Cs_2CO_3$ solution and then drying the product at 130° C. for 2 hours and calcining it at 540° C. for 2 hours. The Cs content is 0.6% by weight.

Catalyst D 200 g of catalyst A are subjected to ion exchange with 1 l of an aqueous solution of 16.7 g of $FeCl_3 \times 6 H_2O$ and 50 g of $NH_4Cl$ for 24 hours at room temperature and then washed Cl-free with $H_2O$, dried at 150° C. for 1 hour and calcined at 500° C. for 2 hours. This powder is molded with finely divided $SiO_2$ in a weight ratio of 70:30, and the extrudates are dried and then calcined at 500° C. for 16 hours.

Catalyst E

Catalyst E is obtained by impregnating the extrudates of catalyst A with an aqueous solution of cerium and palladium nitrate and then drying the product at 130° C. for 2 hours and calcining it at 540° C. for 2 hours. The Ce content is 2.3% by weight and the Pd content 0.5% by weight.

Catalyst F

Catalyst F is prepared similarly to catalyst C, except that $Cs_2CO_3$ is replaced with $Fe(NO_3)_3$. The Fe content is 2.9% by weight.

Catalyst G

Catalyst G is prepared similarly to catalyst C, except that $Cs_2CO_3$ is replaced with $Ni(NO_3)_2$. The Ni content is 3.3% by weight.

Catalyst H

Catalyst H is prepared similarly to catalyst C, except that $Cs_2CO_3$ is replaced with $Ce(NO_3)_3$. The Ce content is 1.65% by weight.

Catalyst I

Catalyst I is prepared similarly to catalyst C, except that $Cs_2CO_3$ is replaced with $Co(NO_3)_2$. The Co content is 3.1% by weight.

Catalyst J

Catalyst J is prepared similarly to catalyst C, except that $Cs_2CO_3$ is replaced with $Cr(NO_3)_3$. The Cr content is 1.9% by weight.

Catalyst K $AlPO_4$-12 (APO-12) is synthesised by dissolving or suspending, respectively, 200 g of 98% strength phosphoric acid and 136 g of boehmite in 400 g of water, adding an aqueous solution of 60 g of ethylenediamine and 320 g of $H_2O$ and reacting this mixture in a stirred autoclave at 200° C. under autogenous pressure for 24 hours. The crystalline material is filtered off and then dried at 120° C. and calcined at 500° C. for 16 hours. The $AlPO_4$-12 synthesised in this manner contains 55.5% by weight of $P_2O_5$ and 39.7% by weight of $Al_2O_3$. This material is molded with extrusion assistants to give 3 mm extrudates, which are dried repeatedly at 120° C. and calcined at 500° C. for 6 hours.

Catalyst L

Silicon aluminum phosphate-5 (SAPO-5) is prepared from a mixture of 220 g of 98% strength phosphoric acid, 136 g of boehmite, 60 g of 30% strength silica sol, 287 g of tripropylamine and 587 g of $H_2O$. This mixture is reacted at 150° C. under autogenous pressure for 168 hours. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion assistant to give 3 mm extrudates, which are dried at 120° C. and calcined at 500° C.

Catalyst M

Commercial zirconium phosphate $Zr_3(PO_4)_4$ molded as a pure substance.

Catalyst N

A commercial L zeolite (Baylith L ®) is molded with boehmite in a weight ratio of 80:20 to give 2 mm extrudates. After drying at 110° C. for 16 hours and calcination at 500° C. for 16 hours, the finished catalyst N is obtained.

Catalyst O $CePO_4$ is obtained by precipitation from 52 g of $Ce(NO_3)_3 \times 6\ H_2O$ and 56 g of $NaH_2PO_4 \times 2\ H_2O$. The material is filtered off and converted to extrudates, which are dried at 120° C. and calcined at 450° C. Catalyst O contains 47.1% by weight of Ce and 12.7% by weight of P.

EXAMPLE 18

200 ml/h of tetramethoxypropane are vaporized in a stream of 300 ml/h of nitrogen and passed, at 220° C., over 1 l of a boron zeolite catalyst A, which is contained in a reaction tube electrically heated from the outside.

The gaseous reaction mixture is passed into the middle section of a fractionating column, and the methanol formed and other low boilers are distilled off via the top, while 3-methoxyacrolein and small amounts of unconverted starting material can be removed from the bottom of the column.

Purification is effected in a simple manner by conventional distillation.

The conversion of tetramethoxypropane is >95% and the distillation yield is 91%.

Catalyst A still shows no signs of deactivation after a reaction time of 85 hours.

EXAMPLE 19

The procedure described in Example 18 is followed, except that tetraethoxypropane is reacted.

The yield of ethoxypropenal is 82% at a conversion of 93%.

EXAMPLE 20

The procedure is similar to that of Example 18, except that the reaction product is passed not into a column but into a receiver containing methanol which has been brought to at least pH 10. The conversion of the tetramethoxypropane used is >95%, and the yield of 3,3-dimethoxypropionaldehyde is 61% of theory.

EXAMPLE 21

Like Example 20, Example 21 relates to the preparation of 3,3-dimethoxypropionaldehyde.

In a stirred apparatus, a solution of 295 g of 3-methoxyacrolein in 175 ml of tetrahydrofuran is slowly added dropwise, at 25° C., to 700 ml of methanol which are brought to pH 12 with 10.3 g of 30% strength methanolic sodium methylate solution. When the addition is complete, stirring is continued for 3 hours at 25° C. The pH is then brought to 7 with dilute sulfuric acid, and the mixture is worked up. 256 g of 3,3-dimethoxypropionaldehyde (bp. =59° C./22 mbar) are obtained, corresponding to a yield of 63% of theory.

EXAMPLE 22

A procedure similar to that described in Example 18 is used and 2,2,4,4-tetramethoxypentane is converted to 4-methoxybut-3-en-2-one, the conversion being >95% and the yield 93%.

EXAMPLE 23

A procedure similar to that described in Example 18 is used and methyl 3,3-dimethoxybutyrate is converted to the 3-methoxycrotonate, the conversion being >95% and the yield 96%.

TABLE 1

| Example | 1 | 2 | 3 | 4 | 5 | 6 | 7 | 8 | 9 |
|---|---|---|---|---|---|---|---|---|---|
| Educt | Tetramethoxypropane saturated with $H_2O$ (~4% by weight) | | | | | | | | |
| Catalyst | B | C | D | E | M | K | L | N | O |
| Temperature | 300° C. | 300° C. | 300° C. | 300° C. | 275° C. | 300° C. | 300° C. | 350° C. | 300° C. |
| WHSV | $2\ h^{-1}$ | $2\ h^{-1}$ | $2\ h^{-1}$ | $2\ h^{-1}$ | $2\ h^{-1}$ | $2.5\ h^{-1}$ | $2.5\ h^{-1}$ | $2.5\ h^{-1}$ | $2.5\ h^{-1}$ |
| Conversion % | 57.8 | 81.8 | 98.8 | 64.1 | 52.4 | 7.0 | 10.9 | 10.3 | 15.5 |
| Selectivity % Methoxyacrolein | 98.3 | 93.0 | 95.7 | 94.5 | 90.5 | 94.3 | 73.4[1] | 86.4 | 94.8 |

[1] plus 3,3-dimethoxypropane with 10% selectivity

TABLE 2

| Example | 10 | 11 | 12 | 13 | 14 |
|---|---|---|---|---|---|
| Educt | Tetramethoxypropane: THF = 75:25% by weight | | | | |
| Catalyst | F | G | H | I | J |
| Temperature | 300° C. | 300° C. | 300° C. | 300° C. | 300° C. |
| WHSV | $2\ h^{-1}$ | $2\ h^{-1}$ | $2\ h^{-1}$ | $2\ h^{-1}$ | $2\ h^{-1}$ |
| Conversion % | 97.4 | 80.1 | 61.2 | 44.9 | 44.1 |
| Selectivity % Methoxyacrolein | 82.8 | 87.3 | 94.8 | 93.4 | 94.5 |

TABLE 3

| Example | 15 | 16 | 17 |
|---|---|---|---|
| Educt | 3,3-dimethoxypropionate: THF = 50:50% by weight | | |
| Catalyst | A | A | B |
| Temperature | 200° C. | 300° C. | 300° C. |

TABLE 3-continued

| Example | 15 | 16 | 17 |
|---|---|---|---|
| WHSV | 2 h$^{-1}$ | 2.5 h$^{-1}$ | 2.5 h$^{-1}$ |
| Conversion % | 100 | 100 | 100 |
| Selectivity % Methyl 3-methoxyacrylate | 95.5 | 91.7 | 92.6 |

We claim:

1. A process for the preparation of a bifunctional compound of the formula (I)

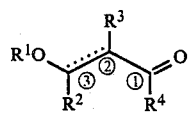 (I)

where $R^1$, $R^2$, and $R^3$ are each alkyl of 1-6 carbon atoms, $R^2$ and $R^3$ may furthermore be hydrogen, $R^2$ may furthermore be alkoxy and $R^4$ is hydrogen, alkyl of 1-6 carbon atoms or alkoxy, and a double bond may be present between carbon atoms 2 and 3, wherein a tetraalkoxyalkan of the formula (11) or a dialkoxyalkanoate of the formula (III)

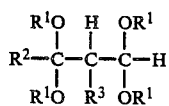 (II)

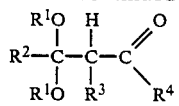 (III)

where $R^1$, $R^2$, $R^3$ and $R^4$ have the above meanings, is converted in the presence of a zeolite as a catalyst.

2. A process as claimed in claim 1, wherein the starting material used is 1,1,3,3-tetramethoxypropane.

3. A process as claimed in claim 1, wherein the starting material used is methyl 3,3-dimethoxypropionate or methyl 3,3-dimethoxybutyrate.

4. A process as claimed in claim 1, wherein the catalyst used is a zeolite of the pentasil type.

5. A process as claimed in claim 1, wherein the catalyst used is an aluminosilicate zeolite.

6. A process as claimed in claim 1, wherein the catalyst used is a borosilicate zeolite.

7. A process as claimed in claim 1, wherein the catalyst used is an iron silicate zeolite.

8. A process as claimed in claim 1, wherein the catalyst used is a zeolite of the faujasite type.

9. A process as claimed in claim 1, wherein the catalyst used is a zeolite doped with an alkali metal, a transition metal or a rare earth metal.

10. A process as claimed in claim 4, wherein the catalyst used is an aluminosilicate zeolite.

11. A process as claimed in claim 4, wherein the catalyst used is a borosilicate zeolite 12. A process as claimed in claim 4, wherein the catalyst used is an iron silicate zeolite.

* * * * *